US006255118B1

(12) United States Patent
Alfano et al.

(10) Patent No.: US 6,255,118 B1
(45) Date of Patent: Jul. 3, 2001

(54) METHOD FOR USING AN ALL SOLID-STATE FLUOROMETER IN INDUSTRIAL WATER SYSTEM APPLICATIONS

(75) Inventors: Joseph C. Alfano; Michael J. Fehr, both of Lisle; Martin R. Godfrey, Elburn; John E. Hoots, St. Charles; Karen R. Tubergen, Mt. Prospect; James E. Whitten; Narasimha M. Rao, both of Naperville, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/224,147

(22) Filed: Dec. 31, 1998

Related U.S. Application Data

(62) Division of application No. 08/873,046, filed on Jun. 11, 1997, now abandoned, and a division of application No. 08/719,507, filed on Sep. 23, 1996, now abandoned.

(51) Int. Cl.$^7$ .................................................. G01N 21/76
(52) U.S. Cl. ............................ 436/172; 436/55; 436/52; 422/82.08; 422/67
(58) Field of Search ................... 422/82.05, 82.07, 422/82.08, 62, 67; 200/458.1; 436/43, 50, 52, 55, 164, 172

(56) References Cited

U.S. PATENT DOCUMENTS

| | | | |
|---|---|---|---|
| 5,116,759 | * 5/1992 | Klainer et al. | 435/288 |
| 5,176,882 | 1/1993 | Gray et al. | . |
| 5,464,587 | 11/1995 | Lippitsch et al. | . |
| 5,691,205 | 11/1997 | Kawabata et al. | . |

FOREIGN PATENT DOCUMENTS 19709377   9/1998   (DE) .

OTHER PUBLICATIONS

Smith et al., "High Precision Fluorimetry with a Light–Emitting Diode Source," Appl. Spectroscopy vol. 42, 1469–1472 (1988).

Imasaka et al., "Visible Semiconductor Laser Fluorometry," Anal. Chem. 61, 2285–2288 (1989).

Patonay et al., "Semioconductor Lasers in Analytical Chemistry," Proceedings of SPIE–The International Society for Optical Engineering vol. 1435, 52–63 (1991).

Higashijima et al., "Determination of Amino Acid By Capillary Zone Electrophoresis Based on Semiondutor Laser Fluoresence Detection," Anal. Chem. 64, 711–714 (1992).

(List continued on next page.)

Primary Examiner—Lyle A. Alexander
(74) Attorney, Agent, or Firm—Margaret M. Brumm; Thomas M. Breininger

(57) ABSTRACT

A solid-state fluorometry instrument is provided. The instrument is based on either diode laser or light-emitting diode (LED) excitation sources that are capable of being used in a wide range of applications. The solid-state diode laser based fluorometer instrument monitors fluorescent tracers, particularly suitable for industrial water sample stream applications. Using the instrument, a solid-state diode laser or light-emitting diode (LED) is used as an excitation source to excite fluorescent tracer molecules. The fluorescence resulting from the diode laser excitation is imaged with a lens onto a silicon photodiode detector. An optical filter is placed between the sample cell and the photodiode detector to reject scattered laser light. The output from the photodiode is amplified to produce an output voltage proportional to the quantity of fluorescence striking the photodiode detector. Since fluorescence is proportional to the concentration of a fluorophore present in the sample stream, continuous monitoring of a voltage output may be performed which further allows real time measurement of concentration of a fluorescent tracer present in, for example, a sample stream.

3 Claims, 10 Drawing Sheets

OTHER PUBLICATIONS

Mank et al., "Visible Diode Laser Induced Fluorescence Detection in Liquid Chromatography after Precolumn Derivatization of Thiols," Anal. Chem. 65, 2197–2203 (1993).

Hauser et al., "A Solid–State Instrument for Fluorescence Chemical Sensors Using a Blue Light–Emitting Diode of High Intensity," Meas. Sci. Technol. 6, 1081–1085 (1995).

Wengatz et al., "Immunoassays for Pesticide Monitoring," Proceedings of SPIE–The International Society for Opitical Engineering 2388, 408–416 (1995).

Williams et al., "Instrument to Detect Near–Infra Red Fluoresence in Solid–Phase Immunoassay," Anal. Chem. 66, 3102–3107 (1994).

Montan et al., "A System for Industrial Surface Monitoring Utilizing Laser–Induced Fluorescence". Appl. Phys. B38, 241–247 (1985).

Winkleman et al., "Quantitative Fluoresence Analysis in Opaque Suspensions Using Front Face Optics," Anal. Chem. 39, 1007–1009 (1967).

T. Araki and H. Misawa, "Light–Emitting Diode–Based Nanosecond Ultraviolet Light Source for Fluorescence Lifetime Measurements," Rev. Sci. Instrum. 66 (12), pp. 5469–5472 (1995).

* cited by examiner

METHOD FOR USING AN ALL SOLID-STATE FLUOROMETER IN INDUSTRIAL WATER SYSTEM APPLICATIONS

CROSS-REFERENCE TO RELATED APPLICATION

This application is a division of U.S. patent application Ser. No. 08/873,046, filed Jun. 11, 1997, now abandoned, and a divisional of Ser. No. 08/719,507, filed Sep. 23, 1996, now abandoned

BACKGROUND OF THE INVENTION

1. Field of the Invention

The present invention generally relates to a system and method for continuously monitoring and controlling concentration of molecules or chemical species. More specifically, the present invention relates to a system and method for monitoring concentration of fluorescent tracer molecules in industrial water systems. Further, the present invention relates to use of an all solid-state diode-laser or light emitting diode-based fluorometer for monitoring the concentration of fluorescent tracer molecules in aqueous, non-aqueous, and mixed aqueous/non-aqueous systems.

2. Description of the Prior Art

It is generally known to use diode lasers or light-emitting diodes (LED) as solid-state excitation sources for fluorescence. The combination, however, of excitation sources with photodiode detectors is not as common. As early as 1988, a fluorometer from an LED and a photodiode detector was constructed. See, for example, an article by Jones et al. entitled "High Precision Fluorimetry with a Light-Emitting Diode Source," *Appl. Spectroscopy* 42, 1469 (1988). In 1989, a 670 nanometer diode laser was used as an excitation source and a pholomultiplier (PMT) as a detector. See Imasaka et al. "Visible Semiconductor Laser Fluorometry," *Anal. Chem.* 61, 2285 (1989). Other examples are known in which semiconductor lasers have been combined with conventional PMT detectors. See, for example, Patonay et al. "Semiconductor Lasers in Analytical Chemistry," *Proceedings of SPIE-The International Society for Optical Engineering* 1435, 42 (1991); Higashijima et al. "Determination of Amino Acid By Capillary Zone Electrophoresis Based on Semiconductor Laser Fluorescence Detection," *Anal. Chem.* 64, 711 (1992); and Mank et al. "Visible Diode Laser Induced Fluorescence Detection in Liquid Chromatography after Precolumn Derivatization of Thiols," *Anal Chem.* 65, 2197 (1993).

In addition, several more recent publications have dealt with fluorescence measurements using LEDs or diode lasers as excitation sources and silicon photodiodes as detectors. See, for example, Hauser et al., "A Solid-State Instrument for Fluorescence Chemical Sensors Using a Blue Light Emitting Diode of High Intensity," *Meas. Sci. Technol.* 6, 1081 (1995); Wengatz et al., "Immunoassays for Pesticide Monitoring," *Proceedings of SPIE-The International Society for Optical Engineering* 2388, 408 (1995); Williams et al., "Instrument to Detect Near-Infra-Red Fluorescence in Solid-Phase Immunoassay," *Anal Chem.* 66, 3102 (1994); and Kawazumi et al., "Laser Fluorimetry Using A Visible Semiconductor Laser and an Avalanche Photodiode for Capillary Electrophoresis," *Anal. Sci.* 11, 587 (1995).

Of the above, most of the few known literature references demonstrate the principle of fluorometry using solid-state, low cost excitation sources. Only a few of the existing papers, however, deal with applications of this instrumentation. For example, Higashijima et al. generally disclose the use of fluorescence detectors for electrophoresis; Mank et al. generally disclose the use of fluorescence detectors for liquid chromatography; and Hauser et al. relate to use of fluorescence detectors for chemical-sensing membranes. In addition, Wengatz et al. explore the use of fluorescence detectors for pesticide monitoring.

A number of other techniques are known for monitoring fluorescence, for example, from oil residues on steel sheets (such as taught by Montan et al. in "A System for Industrial Surface Monitoring Utilizing Laser-Induced Fluorescence," *Appl. Phys.* B38, 241 (1985)) and for fluorescence analysis of biologically important molecules in turbid or opaque tissue samples (for example, as demonstrated by Winkleman et al. in "Quantitative Fluorescence Analysis in Opaque Suspensions Using Front Face Optics," *Anal. Chem.* 39, 1007 (1967)). Furthermore, use of an excimer laser to perform fluorescent imaging of paper surfaces is generally taught by Hakkanen et al. in "Laser-Induced Fluorescence Imaging of Paper Surfaces," *Appl. Spectroscopy* 47, 2122 (1993); and use of a diode laser in surface fluorescence geometry is also generally taught, for example, by German Patent No. DE4300723 A1.

Fluorometers currently being used for industrial process monitoring and control are based on gas-lamp excitation sources and photomultiplier tube detectors which require high current, high voltage power supplies. Additionally, these excitation and detection sources do not have the intrinsic reliability of solid-state semiconductor devices.

A need, therefore, exists for an improved instrument constructed as an all solid-state fluorometer including a system and method for the use of such a fluorometer for monitoring the concentration of fluorescent tracer molecules particularly in industrial water systems.

SUMMARY OF THE INVENTION

The present invention provides for improved devices and methods for monitoring the concentration of molecules and chemical treatments in industrial water sample streams.

To this end, in an embodiment of the present invention, a device is provided having a solid-state excitation source to direct light in a specified direction. A sample having a known concentration of molecules is provided wherein the light from the excitation source is directed at the sample such that the light excites fluorescent tracer molecules in the sample and produces fluorescence. A detector receives the fluorescence from the excitation of the sample and produces an output signal proportional to the quantity of fluorescence received on the detector wherein the quantity of fluorescence is further proportional to the concentration of the molecules in the sample. If the concentration of the fluorophore is proportional to non-fluorescing chemical treatments or additives, then the concentration of the chemical treatments or additives can be monitored.

In an embodiment, a lens, though not crucial, may be provided between the sample and the detector to image the fluorescence excited from the sample onto the detector.

In an embodiment, a filter is constructed and arranged between the sample and the detector to reject scattered excitation light from the sample or sample cell.

In an embodiment, an amplifier is constructed and arranged to receive the signal from the detector to produce an amplified output signal.

In an embodiment, a battery provides power necessary to activate the excitation source and detector circuitry. The excitation source may be a diode laser, a light emitting diode or other solid-state light sources.

In an embodiment, DC power from an AC-DC transformer provides power necessary to activate the excitation source and detector circuitry.

In an embodiment, the sample is a portion of an industrial water stream.

In an embodiment, the tracer molecules are fluorophores.

In an embodiment, the monitoring is conducted in real time.

In an embodiment, the excited light is filtered from the sample before detecting fluorescence.

In an embodiment, the amplified output signal is indicative of the fluorescence.

In an embodiment, the excitation source may be a diode laser or a light emitting diode.

In an embodiment, power is provided to the instrument such that the power allows for portability of the instrument.

In an embodiment, the excitation source is separated from a point at which detecting occurs such that the components are approximately at a 90° angle with respect to each other.

In another embodiment, the excitation source is separated from a point at which detection occurs such that the components are approximately at a 45° angle with respect to each other. This allows fluorescence to be detected from turbid or opaque samples, since it is not necessary for the excitation light to penetrate the sample. This embodiment is useful for turbid streams such as ceramic slurries, pulp slurries, or opaque waste water streams containing high masses of solids.

In an embodiment in which the excitation source and detector are separated by 45° for the detection of fluorescence in turbid samples, multiple filters may be used to suppress scattered excitation light. The polarized nature of diode laser light may also be taken advantage of to reject scattered excitation light by using cross-polarization in the detection path.

In an embodiment, multiple excitation sources and detectors are stacked to measure a corresponding number of multiple analytes in the sample stream.

In an embodiment, the solid-state excitation source is pulsed to enable measurement of the fluorescent or phosphorescent lifetimes of chemical species in the industrial sample stream.

In an embodiment, the solid-state excitation source is pulsed to enable higher peak output power at a given spectral region without damaging the excitation source.

In an embodiment, the excitation source is pulsed and the detector circuitry is "phase-locked" to the frequency of the excitation source to achieve higher sensitivity or to differentiate between multiple excitation sources.

In an embodiment, the concentration of a non-fluorescing chemical treatment or additive can be measured and controlled when it is fed in known proportion to a fluorescing tracer agent which can be directly measured and controlled with this invention.

In an embodiment, near-infrared emitting diode lasers or LEDs are used to excite fluorescence.

In an embodiment, treatment dosage to the sample stream is controlled based on the concentration of molecules detected by the instrument.

In an embodiment, the output signal is monitored continuously and in real time to determine the concentration of molecules.

In one embodiment, leakage to or from a liquid process stream is detected by detecting the concentration of molecules into or from a process, respectively.

It is, therefore, an advantage of the present invention to provide an improved fluorometer instrument.

Another advantage of the present invention is to provide systems and methods which require applications for use of an improved fluorometer instrument.

Yet another advantage of the present invention is to provide an improved fluorometer instrument capable of monitoring multiple fluorescent responses in a liquid process stream.

A still further advantage of the present invention is to provide an improved fluorometer instrument for applications in which fluorescence measurements take place in turbid sample streams.

And, another advantage of the present invention is to provide a fluorometer with improved sensitivity for certain types of fluorescent molecules.

Yet another advantage of the present invention is to provide a fluorometer instrument for use in applications with an ability to perform pulsed laser or LED fluorometry.

A still further advantage of the present invention is to provide a fluorometer for use in applications that require improved reliability.

Yet another advantage of the present invention is to provide a fluorometer instrument that is portable.

Moreover, an advantage of the present invention is to provide a fluorometer instrument for use in applications that require fiber optic capability.

A still further advantage of the present invention is to provide a fluorometer instrument for use in applications requiring the fluorescent or phosphorescent lifetimes of molecules to be measured.

A still further advantage of the present invention is to provide a fluorometer instrument for use in applications that require fluorescence anisotropy.

Additional features and advantages of the present invention are described in, and will be apparent from, the detailed description of the presently preferred embodiments and from the drawings.

The invention detailed in this application is distinct from the prior art, in that it provides for the use of all-solid-state fluorometers for use in monitoring and control of industrial process waters. While the prior art discloses the use of fluorescent monitoring of fluorescent tracer species for monitor and control of industrial processes, it does not teach the use of all-solid-state fluorometers for this purpose. While additional prior art discloses the design and construction of all-solid-state fluorometers for fluorescent measurements, it does not teach the use of this technology for monitor and control of industrial process.

DESCRIPTION OF THE PREFERRED EMBODIMENTS

The present invention generally relates to the use of all solid-state fluorometers in industrial processes. More specifically, the present invention relates to use of diode laser-based or light-emitting diode-based fluorometers to monitor fluorescent tracers or the concentration of fluorescent tracer molecules in industrial water streams.

Figure 1:
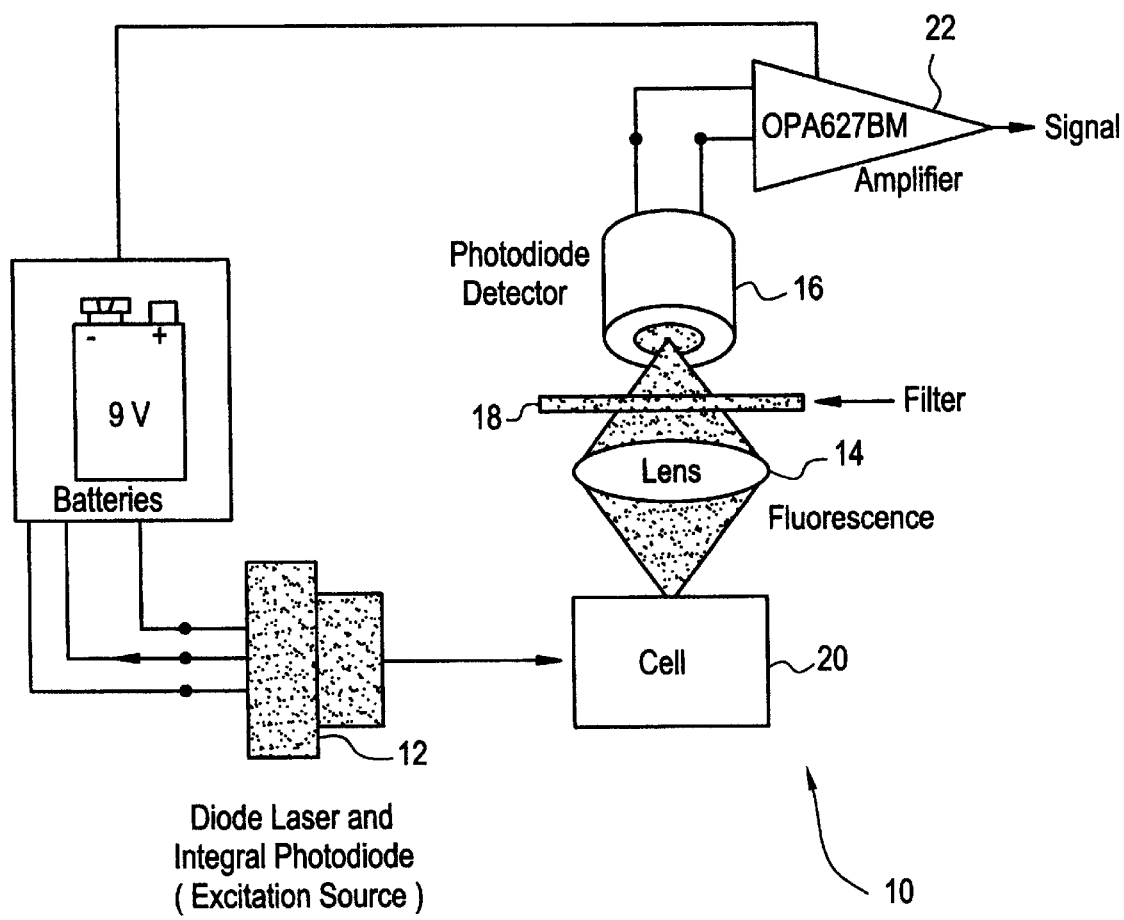
FIG. 1 illustrates a schematic diagram of an embodiment of a fluorometer, using a diode laser excitation source, used in the present invention.

Referring now to FIG. 1, a schematic of an instrument 10 of the present invention is generally illustrated. In the instrument 10, a solid-state diode laser including an integral photodiode 12 is used as an excitation source to excite fluorescent tracer molecules. It should be understood that solid-state lasers emitting visible and near-infrared radiation are presently available and may be incorporated by those skilled in the art.

Fluorescence resulting from excitation of the diode laser 12 may be imaged with a lens 14 onto a silicon photodiode detector 16. (Throughout this disclosure, the term "fluorescence" is meant to encompass both fluorescence and phosphorescence.) An optical filter 18 may be placed between a sample cell 20 and the photodiode detector 16 to reject scattered laser light. An output from the photodiode detector 16 may be amplified by a precision FET-input operational amplifier 22 which is capable of producing an output voltage signal proportional to the quantity of fluorescence-striking the photodiode detector 16.

Since this fluorescence is proportional to the concentration of a fluorophore present in a sample stream, continuous monitoring of a voltage output is possible, and real time measurement of the concentration of a fluorescent tracer present in the sample stream may be ascertained. Furthermore, the voltage signal from the detector 16 may be compared to pre-set values. Such a comparison may take place either electronically or via a microcomputer. With such comparisons, the voltage signal may be used to control a pump relay which is capable of controlling the dosage of a treating agent containing an inert tracer.

The all solid-state diode laser fluorometer instrument 10 of the present invention is suitable for use in several industrial water applications. These include but are not limited to cooling water systems, boiler water systems, pulp slurries, ceramic slurries, mixed solid/liquid systems, and oil-field applications in which polymers with suitable fluorescent tags are used. One cooling water application is inert tracer/treatment actives for closed-loop cooling/heating systems. The diode laser fluorometer instrument 10 may be combined with a suitable tracer molecule and used to monitor and control treatment dosage in closed-loop systems. As a result, on-line chemical feed control, that enables tight control of the amount of chemical in the system as water is added to or removed from the system, may be attained. In addition, monitoring of actives consumption may also be achieved. Since the concentration of the inert tracer yields information on the amount of treatment added to the system, the consumption of the treatment agent may be determined. This information may then be used to make accurate and timely treatment decisions. Further, leak detection may also be achieved. The amount of leakage, either from the cooling stream to a process, or from a process into the cooling stream, may be measured if either of these contain a fluorophore.

Another cooling water application is for C-factor measurements. C-factor is a measure of fouling defined as in the following equation as:

$$C = \frac{Flow}{\sqrt{\Delta P}},$$

where C is the C-factor, Flow is the flow rate of the system and $\Delta P$ is the drop in pressure of the system.

The diode laser fluorometer instrument 10 may be combined with a suitable tracer molecule and used to monitor fouling and constriction of heat-exchanger tubes via measurement of C-factors. These measurements consist of determining the pressure drop across the heat exchanger tube and then measuring the flow rate of the water stream. The diode laser fluorometer instrument 10 and suitable tracer may then be used to ascertain the flow rate by injecting the tracer at some point upstream in the system, and using the diode laser fluorometer instrument 10 to monitor the diluted tracer concentration downstream of the injection point.

Figure 2:
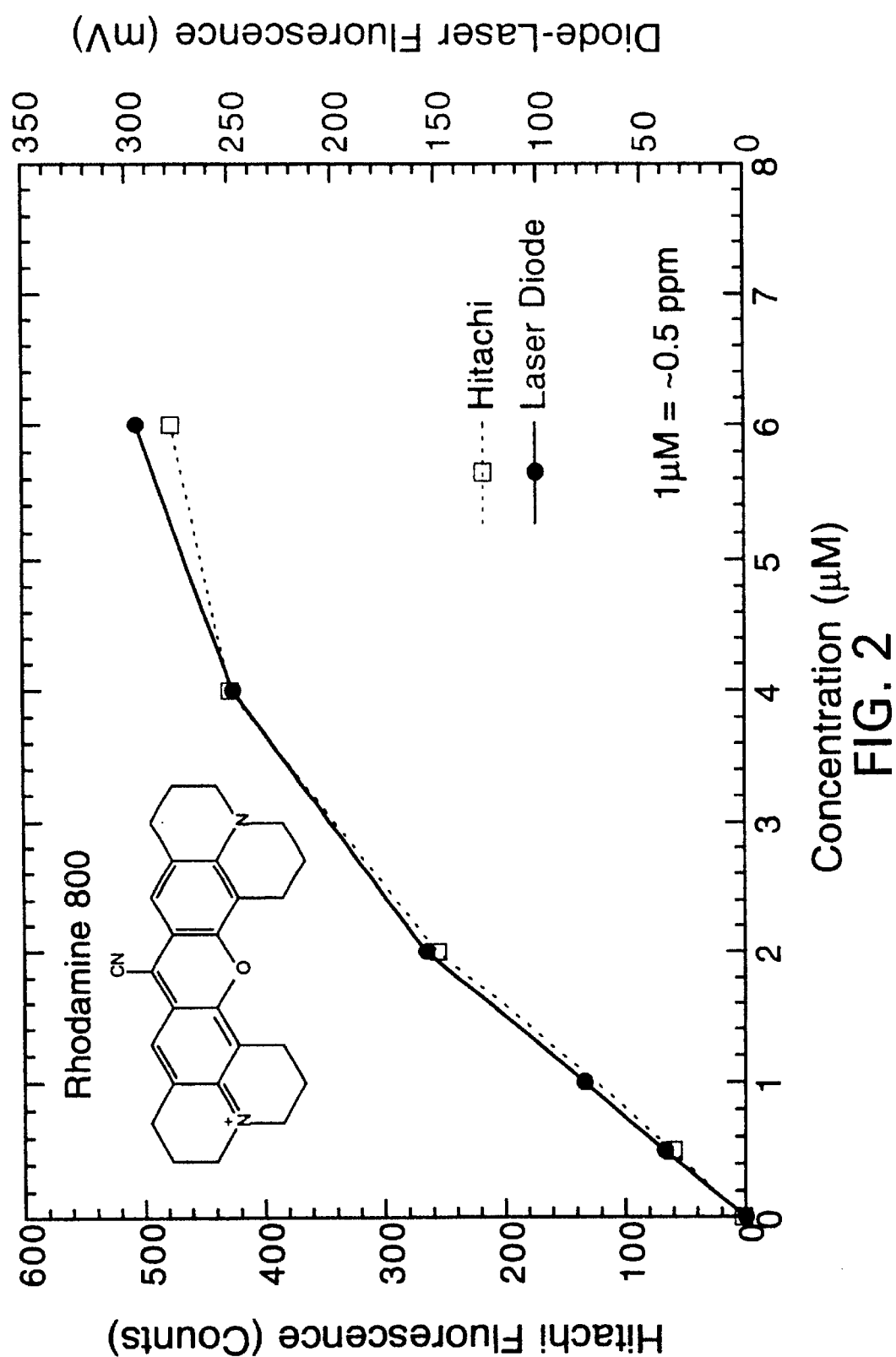
FIG. 2 illustrates fluorescence data from a laser diode fluorometer of the present invention compared to that from a conventional fluorometer.

Another cooling water application involves inert tracer/treatment actives for open circulating systems. When coupled with an inert tracer molecule in open recirculating cooling water systems, the diode laser fluorometer instrument 10 may be used for monitoring, control and system diagnostics in open recirculating cooling water systems. The type of monitoring, control and diagnostics may be similar to those described in the closed-loop cooling/heating systems set forth above. When used to monitor/control inert tracer (treatment dosage) and treatment actives, the diode laser fluorometer instrument 10 may be used to directly monitor/control system consumption of treatment actives. Using existing technology well-known to those of ordinary skill in the art, the fluorometer instrument 10 may be used to measure the fluorescence intensity of a range of fluorescent compounds. An example of a suitable red-absorbing fluorophore is rhodamine 800. A plot of its fluorescence intensity, as measured with the diode laser fluorometer instrument 10, and with a conventionally known fluorometer, is shown in FIG. 2.

In boiler/food processing applications, the solid-state fluorometer instrument may be used for numerous boiler diagnostic monitoring and control applications including chemical feed and control, boiler carry-over studies, boiler holding time measurements, boiler leak detection, and measurement of boiler cycles of concentration. Boiler cycles of concentration are defined herein as the quotient of the concentration of a component in the blowdown and the concentration of that component in the feedwater. Cycles= $C_f/C_i$=(steady state blowdown concentration)/(Feedwater concentration).

This is a critical parameter in boiler operation. If the cycle of concentration value is too high, solubility limits of scale-forming solids can be exceeded. If the cycle value is too low, then there is inefficient usage of water, heat, and treatment chemicals. Fluorescence provides a convenient and accurate means of measuring cycles, since fluorescent molecules do not appreciably carry over into the steam and can be sensitively detected at low concentrations. Boiler holding time is defined in U.S. Pat. No. 5,041,386, column 3, line 47 through column 5, line 14, the disclosure of which is incorporated herein by reference. This time can be an important parameter in applying the treating agent. If the treating agent fluoresces, or if it is fed simultaneously with an inert fluorescing agent, then the holding time can be measured by fluorescence. Further, any treating agent can be monitored if it fluoresces or is fed with a fluorescing agent.

Fluorescein may be used as an additive for boilers which may be particularly beneficial in food applications. Blue light-emitting diodes are presently available which make construction of a solid-state fluorometer for fluorescein possible. Blue diode lasers may be used to greatly increase the sensitivity of the solid-state fluorometer. A laser-based instrument could also be combined with a miniature photo-multiplier tube to provide orders of magnitude more sensitivity than existing instrumentation.

Figure 3:
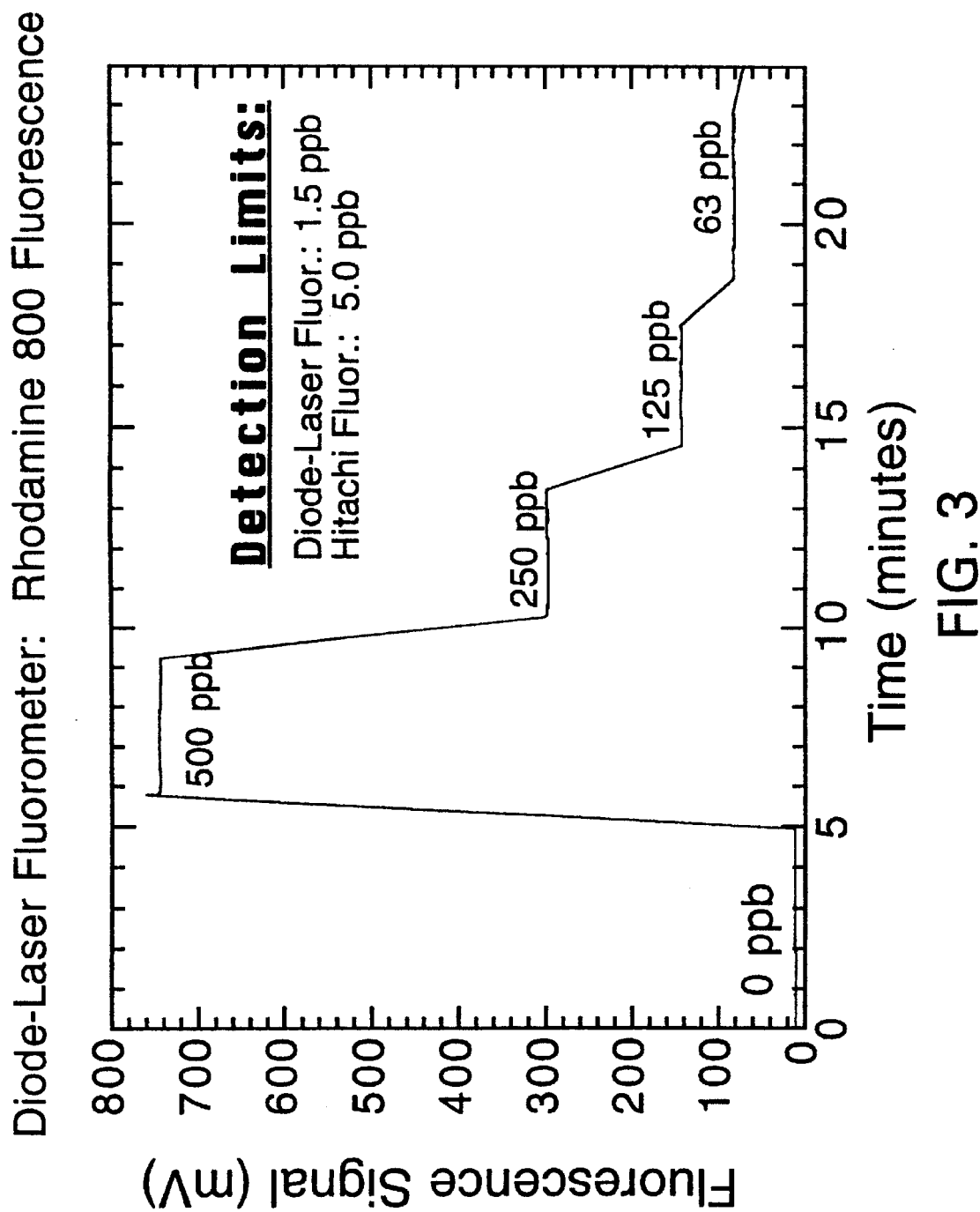
FIG. 3 illustrates a graph of fluorescence from a diode laser fluorometer.

FIG. 3 illustrates the fluorescence signal of the diode laser fluorometer instrument 10 as a function of time for various rhodamine 800 dye concentrations. The detection limit for this dye with the instrument 10 is measured to be 1.5 ppb which is sufficient for the types of applications set forth above.

Figure 4:
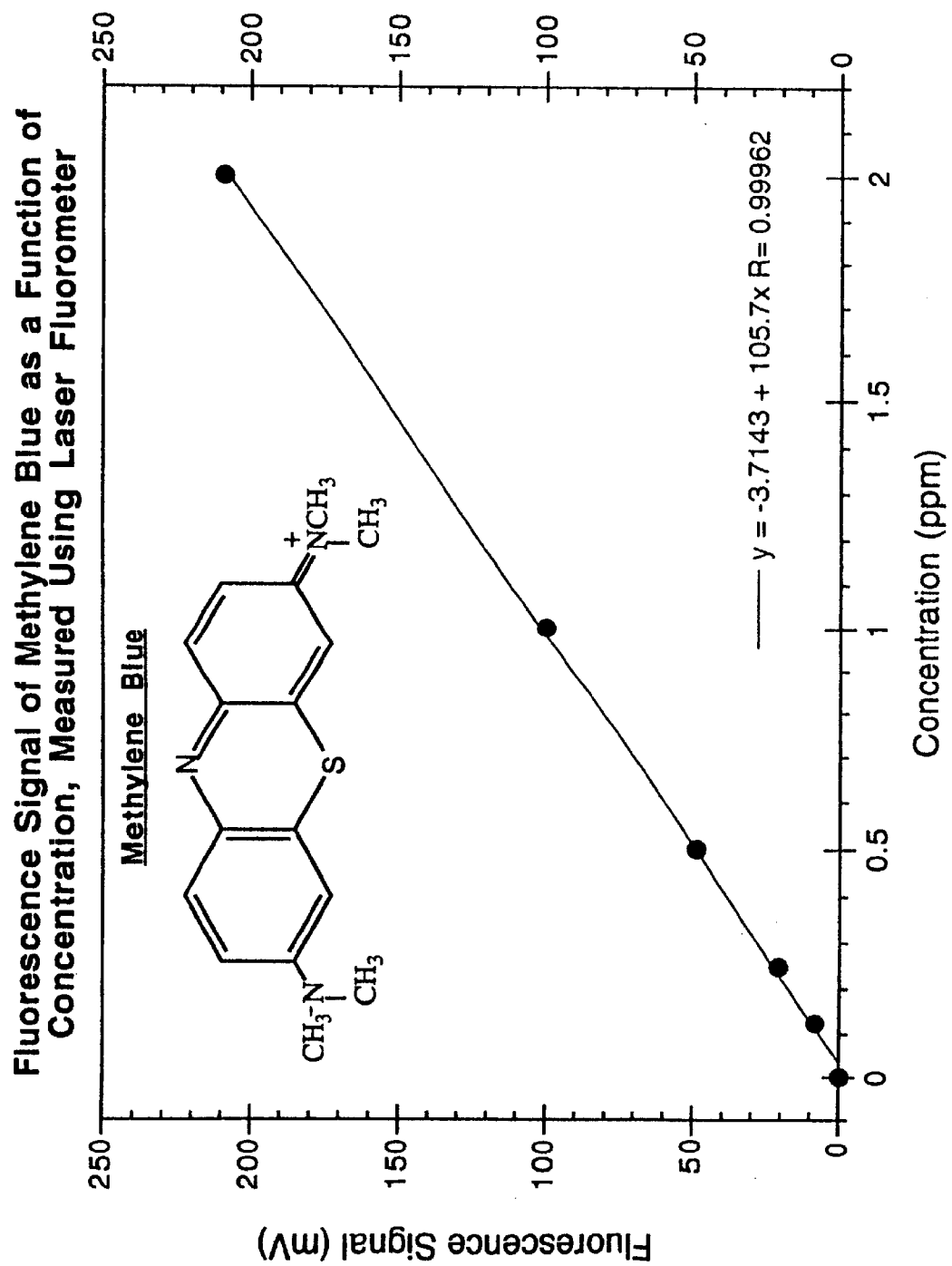
FIG. 4 illustrates a graph of a fluorescence signal of methylene blue as a function of concentration measured using a laser fluorometer.

Another example of a fluorescent compound is methylene blue. FIG. 4 illustrates the fluorescence signal of methylene blue as measured by the diode laser-based fluorometer instrument 10 as a function of methylene blue concentration. The plot is linear with respect to concentration indicating effective performance of the fluorometer instrument 10. The instrument 10 has sufficient sensitivity to measure methylene blue concentrations as low as 10 ppb. Many other dyes may also be implemented which are suitable for fluorescent tracer measurements.

Figure 5:
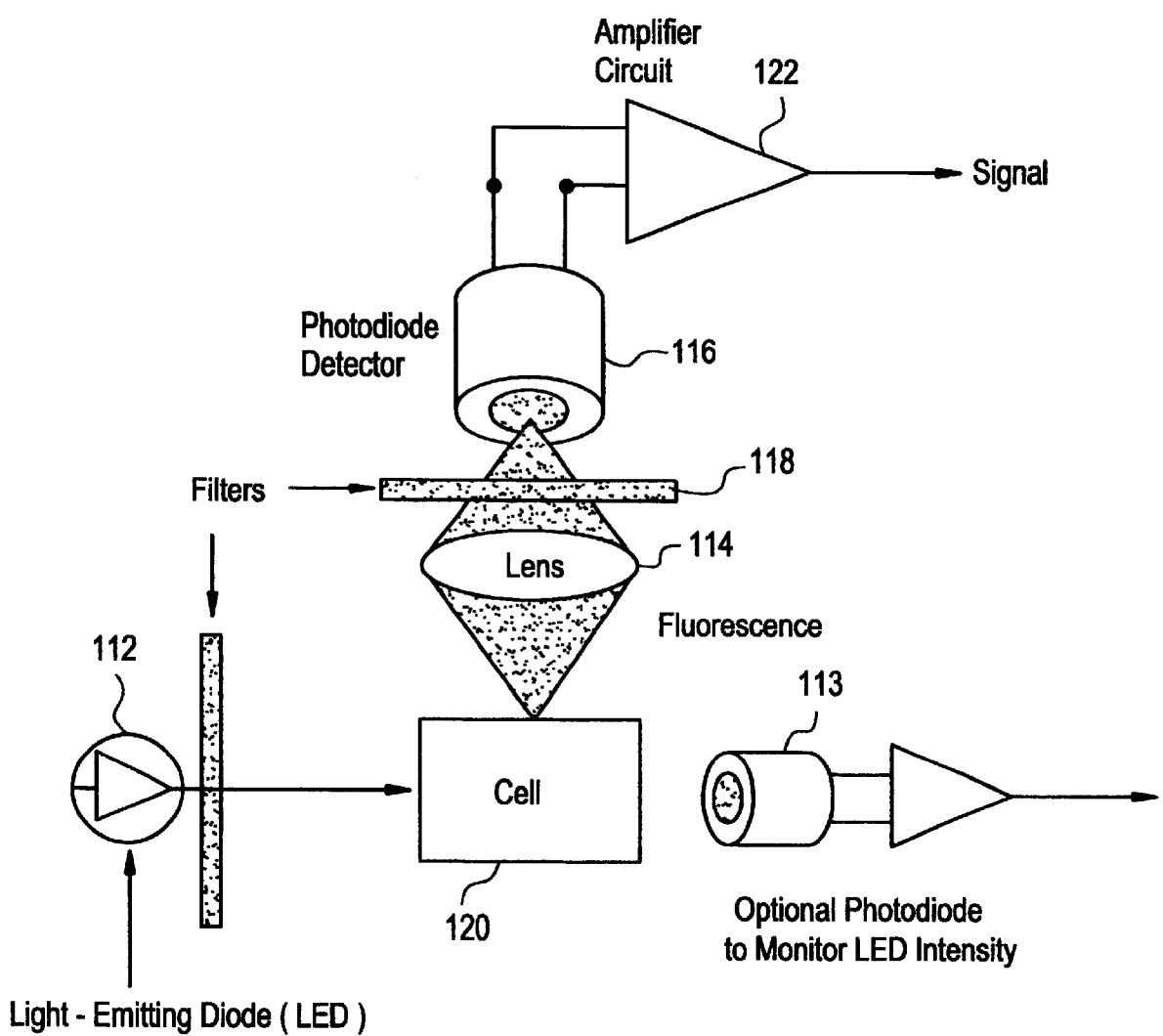
FIG. 5 illustrates a schematic diagram of the embodiment of a fluorometer, using a light-emitting diode as an excitation light source, used in the present invention.

FIG. 5 is a schematic of an embodiment of the present invention in which a light-emitting diode 112 is used as an excitation source. Unlike diode lasers, light-emitting diodes do not have integral photodiodes to monitor and stabilize their optical output. In some cases, as shown in FIG. 5, it may be necessary to use an external photodiode 113 to monitor an output of the light-emitting diode and normalize the fluorescence intensity to variations in its output. This photodiode can also serve as a monitor of optical fouling of the flow cell and can be used to indicate when the cell needs to be cleaned. An optical filter 118 is placed between the light-emitting diode 112 and a sample in order to remove components of the optical output that are at the same wavelength as the fluorescence. Other components of the instrumentation are the same as for FIG. 1.

Figure 6:
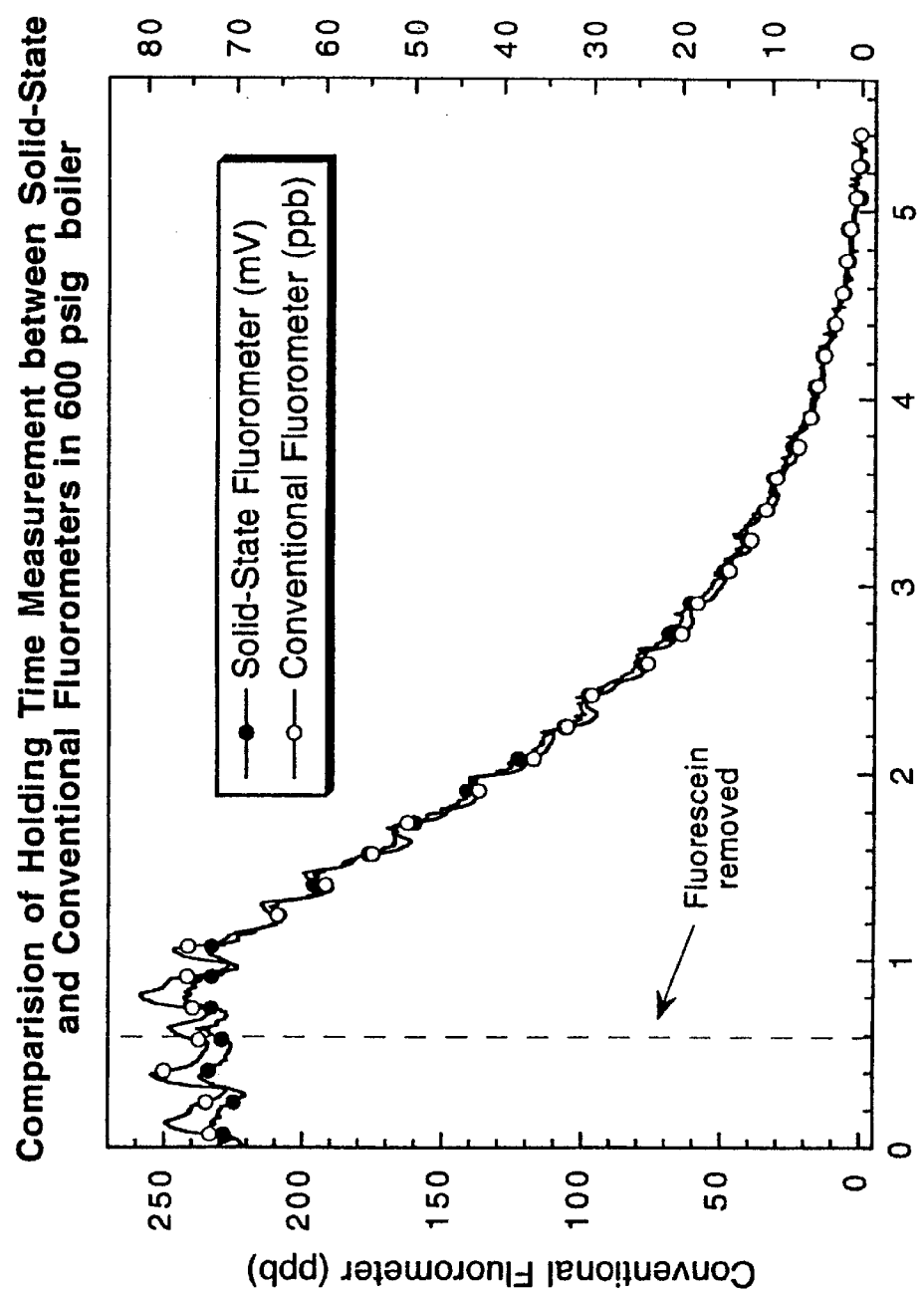
FIG. 6 illustrates a graph of fluorescein fluorescence from a test boiler using the light-emitting diode based fluorometer of the present invention.

FIG. 6 illustrates use of the light-emitting diode fluorometer shown in FIG. 5 to monitor the concentration of fluorescein in a small laboratory simulation boiler. The graph of FIG. 6 shows simultaneous signals from a conventional fluorometer and the solid-state fluorometer equipped with a high brightness blue light-emitting diode with peak emission at 450 nm. The fluorometers are connected in series to the blowdown stream of the boiler. At approximately 0.5 hours into the run, the chemical feed containing the fluorescein was switched off. As shown in FIG. 6, the fluorescence signal decays with time, and the two fluorometers track each other. FIG. 6 illustrates that this invention would perform suitably in boiler water applications.

The use of a solid-state diode laser or light-emitting diode fluorometer to monitor cooling water, boiler, or other industrial water systems, has several advantages over known systems that use conventional fluorometers. For example, a wider application of tracers through reduced equipment costs may be implemented. The cost of the components used to make the instrument 10 of the present invention is significantly lower than the cost of traditional fluorometers which are based on gas discharge lamps and photomultiplier tubes. In addition, the instrument 10 is smaller than current fluorometers. Ideally, the instrument 10 of the present invention may be pocket-sized. Furthermore, power consumption of the instrument 10 is low, less than 0.2 watts and, therefore, the fluorometer instrument 10 may be battery powered. The above monitoring and diagnostics may, therefore, be performed by an individual at a variety of sample points. As a result, a savings in service time is achieved.

In addition to using light-emitting diodes to emit their specified radiation, in some cases LEDs may be used in an unconventional fashion as novel ultraviolet (UV) light sources. Blue LEDs operating at higher than specified forward currents have been found to emit a portion of their optical output in the near-UV region of the spectrum, i.e., in the range of from about 370 nm to about 500 nm. For example, T. Araki and H. Misawa ["Light-Emitting Diode-Based Nanosecond Ultraviolet Light Sources for Fluorescence Lifetime Measurements," Rev. Sci. Instrum. 66,5469 (1995)] have shown that a nominal 450 nm InGaN/AlGaN LED operating at currents greater than 50 mA emits a 380 nm satellite peak which grows in intensity with increasing current.

Satellite emissions of 380–390 nm have been observed from a variety of blue LEDs at higher than specified operating currents and voltages. This satellite peak may be used to excite fluorescence from near-UV absorbing fluorophores for industrial water stream applications, such as pyrene tetrasulfonic acid (PTSA). The LED may either be operated in continuous or pulsed mode. The pulsed mode may be desirable to extend the lifetime of the LED or to allow higher peak optical output to be achieved.

Since the instrument 10 of the present invention is solid-state, this instrument 10 has extremely high reliability. Operating lifetimes of diode lasers are typically between 20,000 to 40,000 hours, which are several times higher than that of gas discharge lamps. Additionally, due to the solid-state nature of the components, the design of the instrument 10 is simpler than conventional instruments and assembly costs are minimal.

The detection limit for rhodamine 800, a red-absorbing fluorophore, was measured at 1.5 ppb with the diode laser fluorometer instrument 10 of the present invention as set forth above. Detection limits for other known fluorometers, such as Hitachi's F4500 Research Fluorometer, is approximately 5 ppb, higher than that of the present invention. Therefore, due to the high sensitivity of the photodiode detector to red light, as well as the high optical efficiency of using monochromatic lasers for an excitation source, the diode laser fluorometer instrument 10 of the present invention has excellent sensitivity. Preferably, the diode laser uses a near infrared wavelength of from about 635 nm to about 1600 nm.

Still further, the small size of the light source and detector of the present invention lends the diode laser fluorometer instrument 10 to multi-channel, multi-analyte detection. A sample stream may contain several fluorescent tracers, and an array of two or more diode lasers of different wavelengths could simultaneously monitor several tracers as the sample stream passes through the flow cell. This type of multi-channel detection is more difficult to achieve using current technology.

In cooling water applications, the fluorometer instrument 10 provides the major advantages of increased sensitivity in portions of the visible spectrum and ability to measure multiple analytes simultaneously, either by stacking light sources and detectors, or by operating the instrument in pulsed mode.

Furthermore, an embodiment of the invention in which the excitation and detection of fluorescence occurs from the front surface of the sample cell makes it possible to perform measurements in sample streams of high turbidity.

By separating the excitation source and detector by 45°, fluorescence can be measured from the surface of the opaque sample or slurry. The coherence and polarization of a laser beam allows the surface fluorometry to be performed much more conveniently and compactly than is possible with conventional excitation sources.

Figure 7:
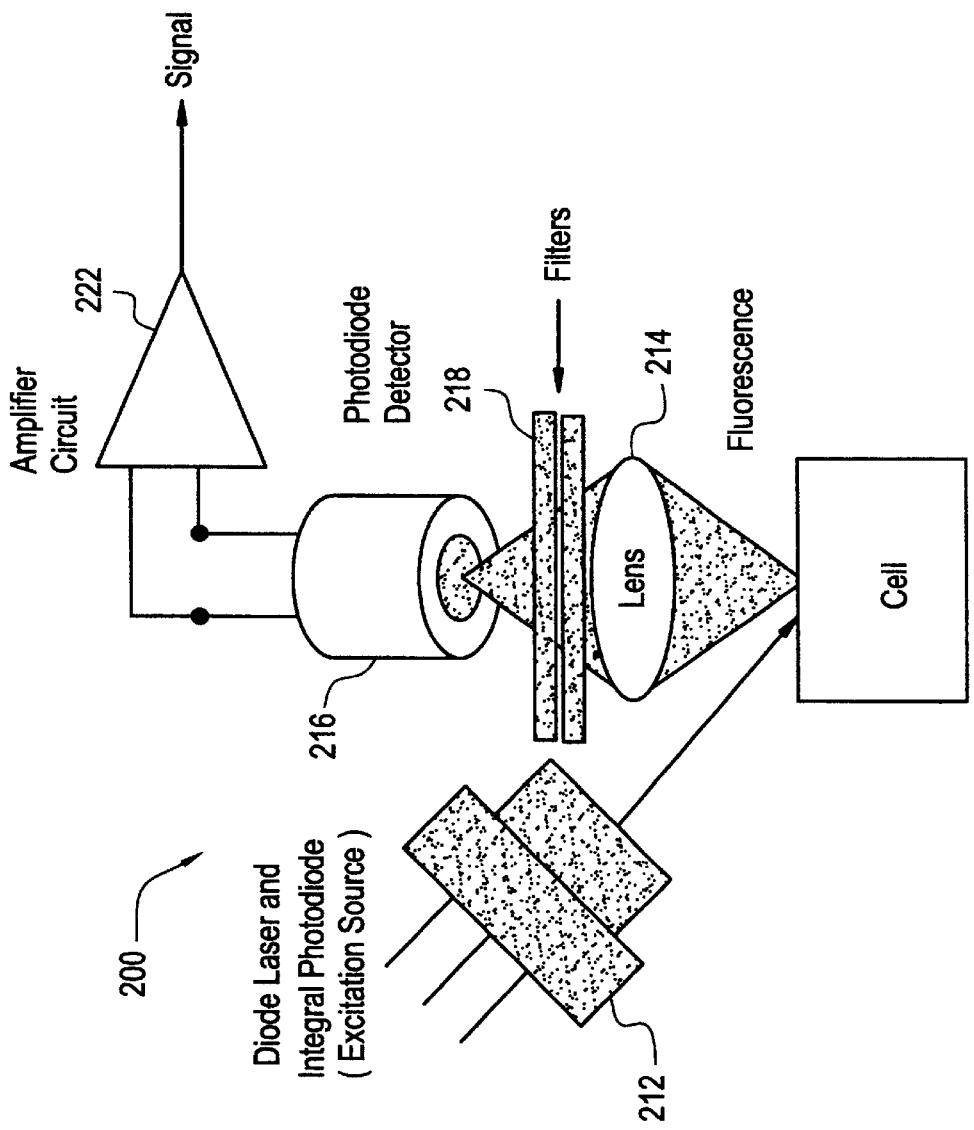
FIG. 7 illustrates a schematic diagram of an embodiment of a fluorometer used for the detection of fluorescence from turbid samples or turbid sample streams.

FIG. 7 illustrates a solid-state fluorometer 200 for detecting surface fluorescence. FIG. 7 shows a diode laser 212 with integral photodiode used as an excitation source. However, a light emitting diode focused by a lens could, as well, be implemented.

In ceramics applications, the solid-state fluorometer instrument 200 in the surface fluorescence configuration may monitor the concentration of fluorescence molecules in ceramic slurries. Applications within ceramic slurries include monitoring of treatment dosages; measurement of mixing times in batch mixing vessels; determination of batch contamination from ball mills and other mixing vessels; and, efficiency of transfer from ball mills to mixing tanks.

Figure 8:
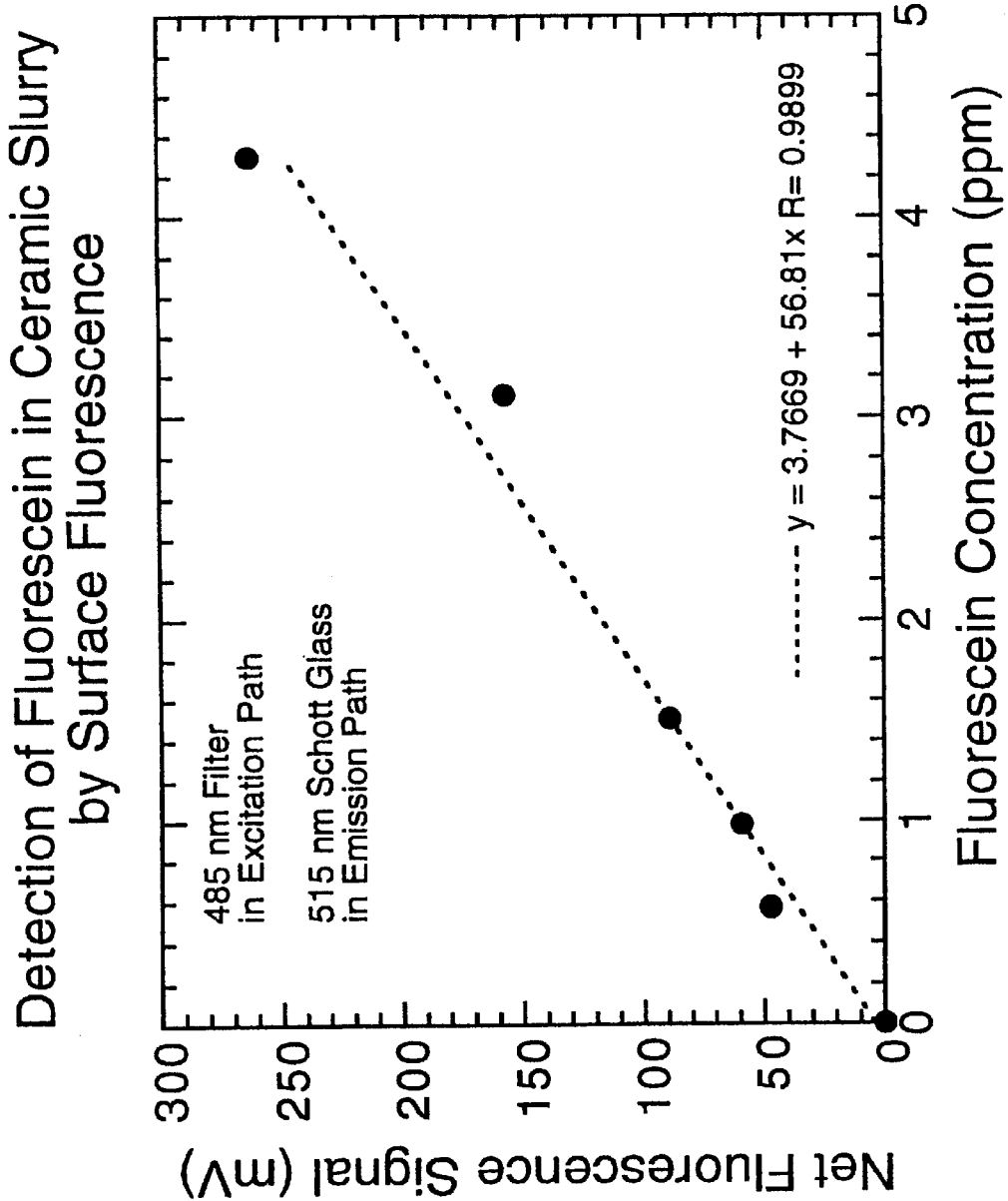
FIG. 8 illustrates a graph of fluorescence from an opaque ceramic slurry using the present invention.

FIG. 8 illustrates the use of the invention in a surface fluorescence embodiment to monitor the concentration of fluorescein in a ceramic slurry.

In solids/liquids separation applications, the solid-state fluorometer instrument 200 in the surface configuration is capable of monitoring the concentration of fluorescent tracer species in solids/liquids waste water and sludge slurries. These slurries are highly turbid and cannot be monitored with current instrumentation without employing laborious filtration methods. These fluorescent measurements may enable a host of solids/liquids applications to be performed, including dosage control and optimization and performance monitoring. The use of the present invention may also be used in mining, such as for coal flocculation and alumina processing where opaque slurries are generated.

Figure 9:
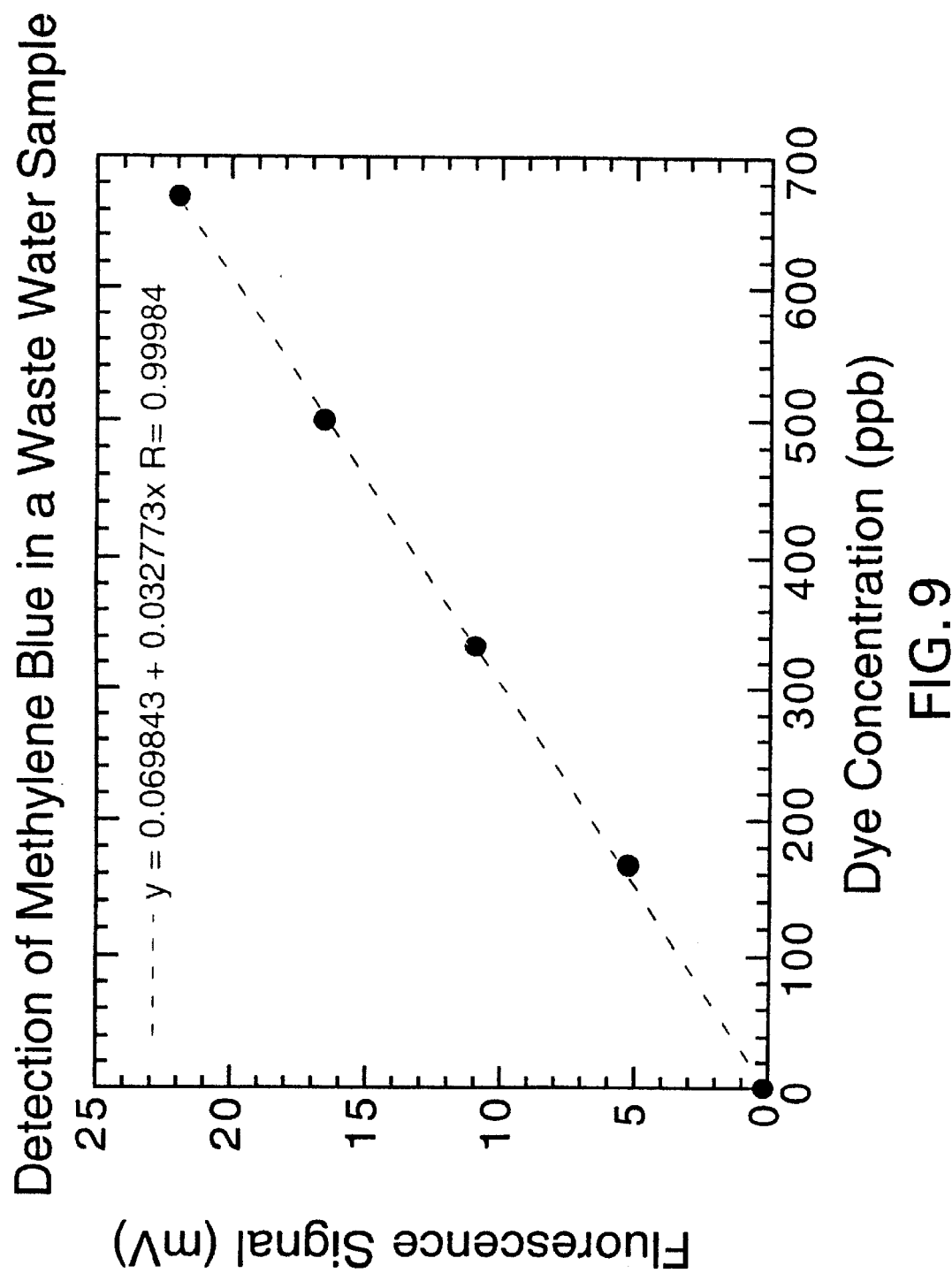
FIG. 9 illustrates a graph of fluorescence from a turbid solids/liquids waste sample using the present invention.

The detection of methylene blue tracer in a turbid waste water sample by surface fluorescence is illustrated in FIG. 9.

In pulp and paper applications, the solid-state fluorometer instrument 200 in the surface configuration monitors fluorescent tracer concentrations in pulp and paper furnishes and pulp slurries. The solid-state fluorometer instrument 200 may be used in such applications to provide easy, inexpensive on-line monitoring capabilities.

Figure 10:
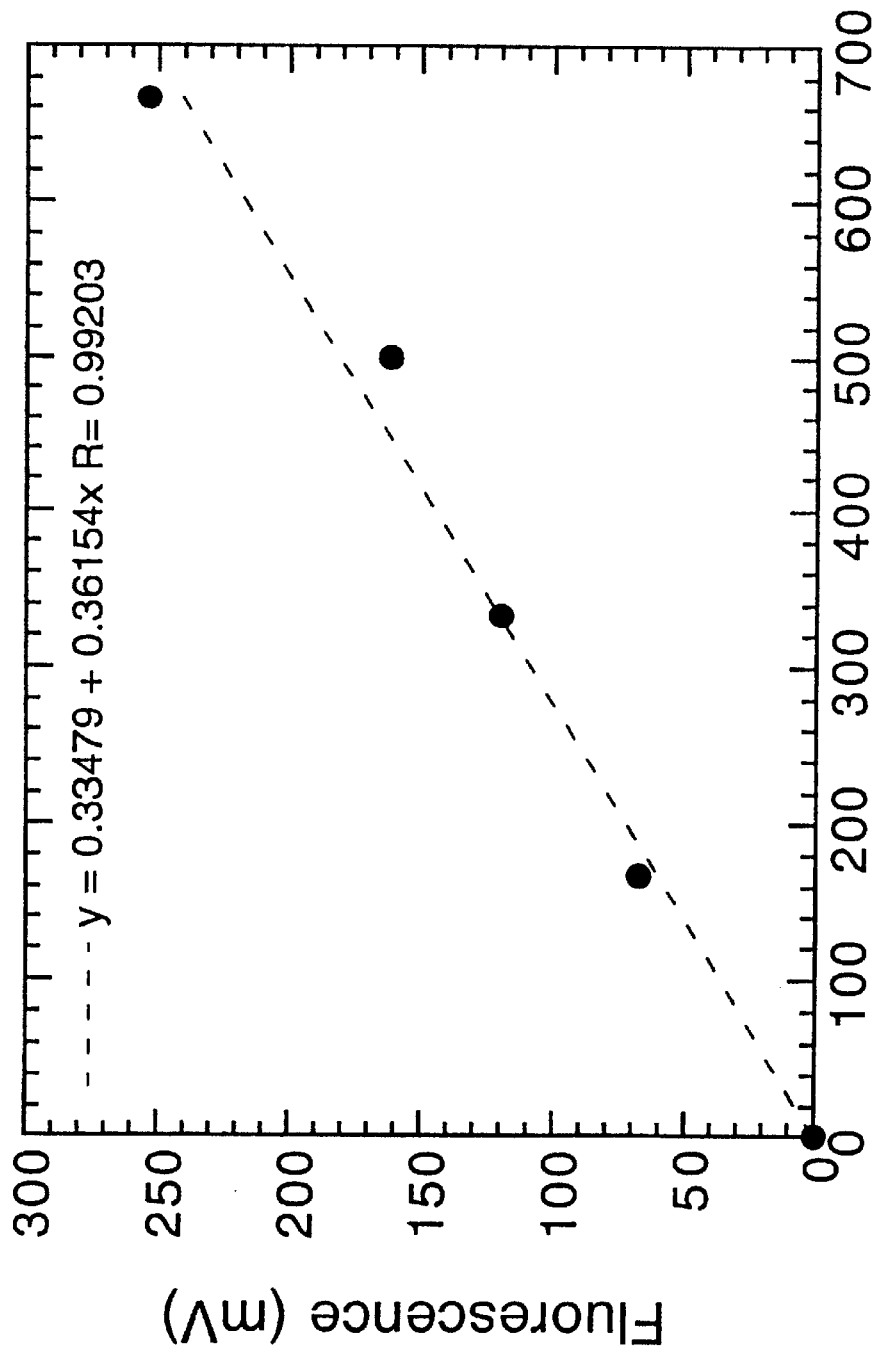
FIG. 10 illustrates a graph of fluorescence from an opaque pulp slurry using the present invention.

FIG. 10 illustrates the detection of methylene blue in a 2.5% pulp slurry by the surface fluorescence embodiment of this invention.

Furthermore, the solid-state fluorometer instruments 10 and 200 may be used in applications including process control and monitoring and determination of treatment dosage via direct monitoring of fluorescent tagged polymers, particularly in specific chemical applications. The disclosure of which is incorporated herein by reference, U.S. Pat. No. 5,171,450 discloses the application of fluorescent tagged polymers.

It should be understood that the solid-state fluorometer instruments 10 and 200 are capable of performing any function of the existing technology provided that a suitable fluorophore is available which absorbs in the range accessible with diode lasers or light emitting diodes.

The capability for multi-analyte analysis and monitoring is achieved due to the fact that the LED's and diode lasers are extremely small, and several of these can be stacked so that multiple analyses with one sample cell can be performed. Silicon photodiode detectors are also small, and a compact instrument capable of detecting multiple tracer molecules simultaneously is possible. Furthermore, the small size and portability of the present invention makes multiple site analysis practical. The capability to monitor the system influent and effluent makes feed-forward as well as feedback control more convenient.

Because diode lasers and LEDs are monochromatic, directional light sources, when used in combination with a suitable tracer molecule, they may give lower detection limits than those achievable using current technology. Improved detection limits allow the use of lower tracer molecule concentrations.

Diode lasers are also capable of being pulsed at high frequencies. With gated detection, pulsed operation allows different fluorophores that have distinct fluorescence lifetimes, but the same or similar absorption/emission spectra, to be resolved. This aids in multi-analyte monitoring. This sort of pulsed operation also permits quantitative detection of non-fluorescing molecules that cause changes in the lifetime of fluorescing tracer molecules. Furthermore, time-resolved fluorescence is capable of differentiating bound versus unbound fluorophores.

Solid-state light sources are intrinsically more reliable than conventional gas discharge lamps used in known fluorometers. Additionally, diode lasers have integral photodiodes for stabilization of their light emission, eliminating the need for mechanical light chopping. This further leads to improved reliability. Unlike conventional gas-discharge lamps, diode lasers and LEDs operate on less than ten volts. This is an advantage in harsh, industrial settings where high humidity can lead to electrical arcing and instabilities in high voltages. The simple design of the solid-state fluorometer instrument 10 (e.g. all solid-state components, no moving parts or high voltage power supply) permits instruments that are portable, smaller and more reliable than existing technology.

Because the solid-state instrument 10 uses small light sources and detectors and does not require high voltage power supplies, it may be constructed to be palm-sized and battery operated as set forth above. As a result, portability of the instrument 10 aids individuals making fluorescence measurements with the same instrument 10 at a variety of sample points.

The implementation of lasers, which are coherent light sources, allows them, via the coherence, to be more easily and efficiently coupled into fiber optics. The use of fiber optics allows the instrument 10 to be constructed with a probe that can conveniently be inserted directly into a sample or sample stream. This direct contact with the solution may have advantages in terms of performance (less light scatter and better signal-to-noise) and reliability (no glass flow cell to break).

Because diode lasers are polarized, the potential of fluorescence polarization to examine bound versus unbound fluorophores in coagulation and flocculation exists. This also allows for optimizing the performance of polymers in solids/liquids separations.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A method for monitoring concentration of chemicals in industrial water systems, the method consisting essentially of the steps of:
   a) providing a solid state fluorometer, wherein said fluorometer comprises:
      i) a solid-state excitation source to direct light in a specified direction, wherein said excitation source is either a light emitting diode, with said light emitting diode emitting light having a wavelength of from about 370 nm to about 500 nm, or a solid state diode laser having an integral photodiode, with said laser emitting light having a wavelength of from about 635 nm to about 1600 nm;
      ii) a detector receiving the fluorescence from the excitation of the sample and producing an output signal proportional to the quantity of fluorescence received on the detector, wherein said detector is a silicon photodiode;
      iii) a sample chamber which is a cell, where the entrance to the cell is not covered by a species-selective membrane;
   b) providing an industrial water system, wherein a chemical treatment or additive has been added to said industrial water system, wherein a fluorescent tracer is present in said chemical treatment or additive in a known proportion to said chemical treatment or additive;
   c) using said fluorometer to detect the fluorescence of the fluorescent tracer in the industrial water system;
   d) programming said fluorometer to produce an output signal proportional to the detected fluorescence; and
   e) controlling dosage of chemical treatments or additives to the industrial water system based on the concentration of fluorescent tracer detected by said fluorometer.

2. The method of claim 1 wherein said solid-state excitation source is a light emitting diode that emits a light having a wavelength of from about 370 nm to about 500 nm.

3. The method of claim 1 wherein said solid-state excitation source is a laser that emits a light having a wavelength of from about 635 nm to about 1600 nm.

* * * * *

UNITED STATES PATENT AND TRADEMARK OFFICE
CERTIFICATE OF CORRECTION

PATENT NO. : 6,255,118 B1
APPLICATION NO. : 09/224147
DATED : July 3, 2001
INVENTOR(S) : Joseph C. Alfano et al.

Page 1 of 1

It is certified that error appears in the above-identified patent and that said Letters Patent is hereby corrected as shown below:

On the Title Page, Item (62):

Delete ", and a division of application No. 08/719,507, filed on Sep. 23, 1996, now abandoned".

In the Specification:

At column 1, line numbers 9-10, delete ", and a divisional of Ser. No. 08/719,507, filed Sep. 23, 1996, now abandoned".

Signed and Sealed this
Ninth Day of September, 2014

Michelle K. Lee
*Deputy Director of the United States Patent and Trademark Office*